United States Patent [19]

Karimi et al.

[11] Patent Number: 5,605,837
[45] Date of Patent: Feb. 25, 1997

[54] CONTROL SOLUTION FOR A BLOOD GLUCOSE MONITOR

[75] Inventors: Saker A. Karimi, Milpitas; Geoffrey McGarraugh, Scotts Valley; Yeung S. Yu, Pleasanton, all of Calif.

[73] Assignee: LifeScan, Inc., Milpitas, Calif.

[21] Appl. No.: 601,386

[22] Filed: Feb. 14, 1996

[51] Int. Cl.⁶ ............................................. G01N 31/00
[52] U.S. Cl. ................... 436/14; 436/8; 436/16; 435/14; 252/408.1
[58] Field of Search ................... 436/8, 14, 16, 436/18; 422/56, 61; 435/14; 252/408.1; 423/449.1

[56] References Cited

U.S. PATENT DOCUMENTS

| | | | |
|---|---|---|---|
| 3,558,522 | 1/1971 | Louderback et al. | 436/10 |
| 3,920,580 | 11/1975 | Mast | 436/14 |
| 3,960,740 | 6/1976 | Truett | 252/73 |
| 4,729,959 | 3/1988 | Ryan | 436/14 |
| 4,935,346 | 6/1990 | Phillips et al. | 435/14 |
| 5,028,542 | 7/1991 | Kennamer et al. | 436/14 |
| 5,187,100 | 2/1993 | Matzinger et al. | 436/16 |
| 5,296,377 | 3/1994 | Rapkin et al. | 436/13 |
| 5,304,468 | 4/1994 | Phillips et al. | 435/14 |
| 5,306,623 | 4/1994 | Kiser et al. | 435/14 |
| 5,308,767 | 5/1994 | Terashima | 436/12 |

OTHER PUBLICATIONS

The Condensed Chemical Dictionary–10th edition, 1981, pp. 502–503.

*Primary Examiner*—Jill Warden
*Assistant Examiner*—Maureen M. Wallenhorst
*Attorney, Agent, or Firm*—James Riesenfeld

[57] ABSTRACT

A control solution for use with a photometric blood glucose strip contains glucose in an aqueous suspension of carbon black. The control solution mimics blood when applied to a whole blood glucose test strip, which is then inserted into a meter. A meter reading within a predetermined range indicates that meter and strip are operating satisfactorily. Preferably the control solution is buffered to a neutral pH and includes chloride ion to provide a stable end point for the glucose reaction. Depending on the glucose concentration, the solution checks meter and strip operation at high, low, and normal blood glucose levels.

16 Claims, 2 Drawing Sheets

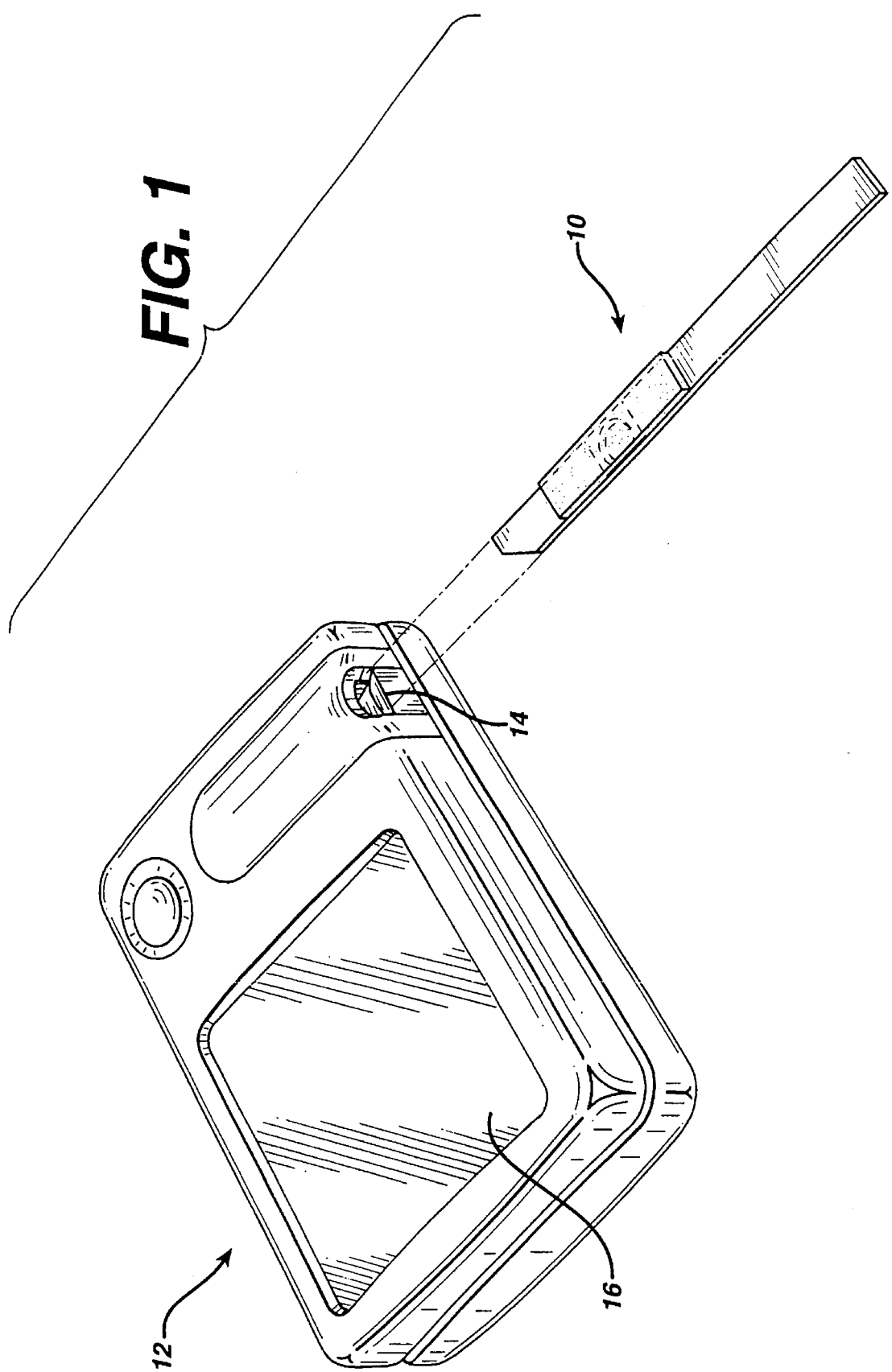

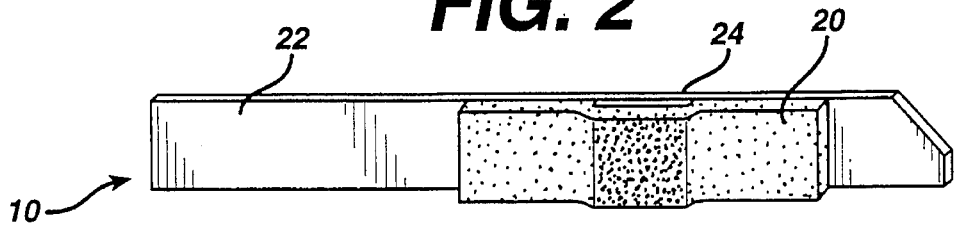
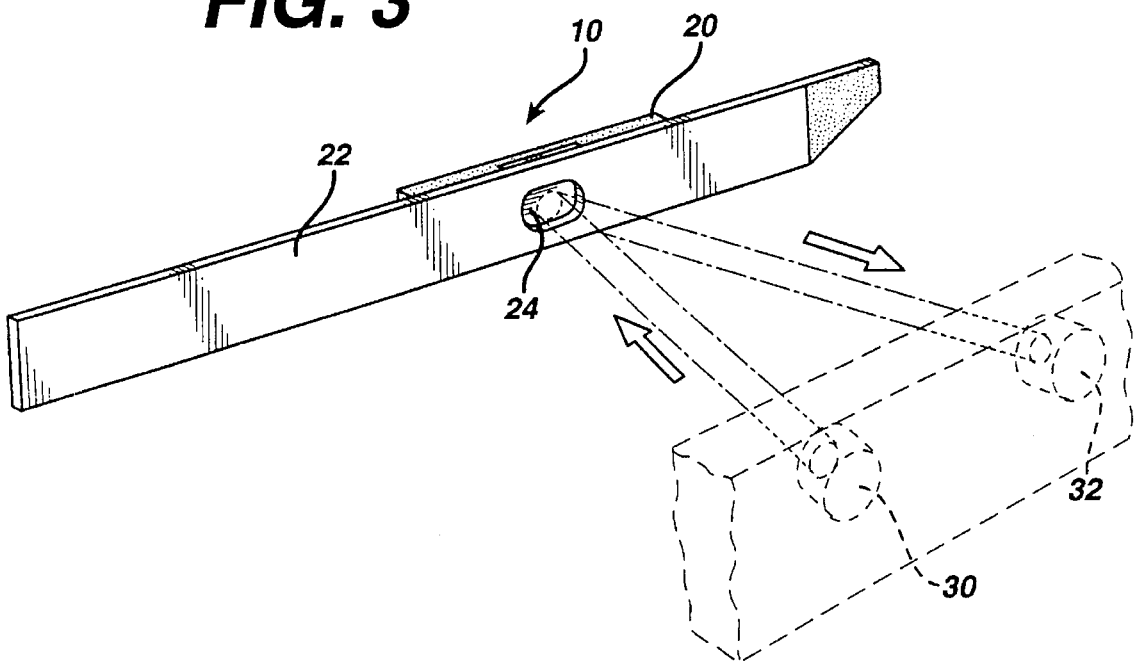

CONTROL SOLUTION FOR A BLOOD GLUCOSE MONITOR

BACKGROUND OF THE INVENTION

1. Field of the Invention

This invention relates to an aqueous dispersion of particles that mimics whole blood when applied to a reagent test strip; more specifically, an aqueous dispersion that can serve as a control solution for a photometric blood glucose measurement system.

2. Description of the Related Art

Reagent strips are quite popular for use in colorimetric reactions, in which strip color is read by a hand-held meter. Specifically, reagent strips are useful in determining the level of analytes, such as glucose, in blood. In practice, whole blood samples are placed on the reagent strip, and after reaction with components incorporated in the strips, a color change permits the determination of glucose levels. Meters, such as blood glucose meters, and reagent strips, such as glucose reagent strips, vary in accuracy and precision. It is therefore necessary to provide a monitoring agent, a "control solution", which determines whether meters and strips are providing accurate values for glucose levels. Of course, it is important to have this solution act in as close as possible a mariner to the sample, i.e., whole blood.

U.S. Pat. No. 5,187,100, issued Feb. 16, 1993 to D. P. Matzinger et al. discloses a control solution for use in a blood glucose measurement system that uses a porous membrane-based reagent strip. The system is adapted to measure concentrations of glucose in whole blood in the presence of optically visible hemoglobin. The control solution comprises a dispersion of a non-water soluble polymer in water, coupled with controlled levels of glucose. Polyvinyl acetate is a preferred polymer.

The control solution of Matzinger et al. is adapted for use in ONE-TOUCH® blood glucose meters, which measure reflectance from a reagent strip at 635 nm and 700 nm. It is not suitable for use in the newer SURESTEP™ blood glucose meters, which measure strip reflectance at 660 nm and 940 mm.

SUMMARY OF THE INVENTION

The present invention provides a control solution for use with a photometric blood glucose strip. The solution mimics whole blood and comprises a suspension of opaque particles in water, a dispersant to keep the particles in suspension, and a predetermined concentration of glucose. In use, the solution is applied to a suitable photometric blood glucose strip, which is inserted into a meter to obtain a reading of glucose concentration. When the meter reading is within the range that is appropriate for a particular control solution, then a user of the meter and strip system can be confident that the system will provide accurate values of glucose concentration in whole blood samples that are applied to the strip.

BRIEF DESCRIPTION OF THE DRAWINGS

FIG. 1 is an exploded perspective view of a strip and meter system that can be used with the control solution of this invention.

FIG. 2 is a plan view of the sample side of the strip of FIG. 1.

FIG. 3 is an exploded, perspective schematic of the optical arrangement of the system of FIG. 1.

DETAILED DESCRIPTION OF THE INVENTION

Although a control solution for a whole blood glucose meter must mimic whole blood, different meter/strip systems identify blood in different ways. Thus, a control solution must mimic blood in a way that is suited to the particular meter and strip. The control solution of the present invention is particularly adapted for use with the SURESTEP™ system, manufactured by the assignee of this invention.

FIG. 1 is an exploded view of a SURESTEP™ meter and strip. Strip 10 is adapted to be inserted into an opening 14 of meter 12. Meter 12 has on its top surface a screen 16 on which the results of the glucose measurement are displayed. The screen can also display instructions, error warnings, and other messages.

FIG. 2 is a plan view of the sample side of the strip of FIG. 1. Strip 10 comprises a transport medium 20 and a support 22 that sandwich test pad 24. In order to determine blood glucose concentration, a sample of whole blood is applied to transport medium 20. The sample passes through the transport medium to test pad 24, which is preferably a hydrophilic anisotropic membrane. The surface of the membrane that adjoins transport medium 20 has large pores—typically in the range from about 30 micrometers to about 40 micrometers. The blood enters the membrane through the large-pore ("sample") surface and travels toward the opposite, small-pore ("testing") surface. As the blood passes through the membrane, the red blood cells become trapped and the glucose-containing plasma passes through. As the sample passes through the membrane, glucose in the sample reacts with a reagent that is impregnated within the membrane to form a light-absorbing dye near the testing surface.

FIG. 3 shows schematically the optical arrangement of the meter and strip of FIG. 1 after the strip has been inserted into the meter. Light source 30 is directed at the testing surface of test pad 24. The light reflected from the testing surface is detected by detector 32. Although, for simplicity, only one light source 30 is shown in FIG. 3, the SURESTEP™ meter incorporates two light-emitting diodes, which emit radiation at 940 nm and 660 nm, respectively.

The 940 nm radiation is used primarily to determine whether the strip has been inserted properly into the meter and whether enough blood has been applied to the strip. Thus, for example, the absorbance by blood of 940 nm radiation causes a reduction in 940 nm radiation detected, which signals to the meter that a sample has been applied to the strip. If insufficient sample has been applied, then there is a smaller change in 940 nm radiation, and an error warning informs the user that not enough blood was applied to the strip.

The 660 nm radiation detects the absorption of the dye that is formed as a result of the interaction of the reagent in the strip with glucose in the blood. As the reaction progresses, more dye is formed, and the 660 nm radiation reflected to the detector decreases. If the system is operating properly, the strip reflectance at 660 nm reaches a substantially constant value at a level indicative of the glucose concentration in the sample. If a constant reflectance is not achieved after a predetermined time period (the period depends on ambient temperature), then an error war, Ling appears.

Based on the above description, it is clear that a control solution for use with the SURESTEP™ system must meet at least these three requirements: First, absorption at 940 nm must be in the range of absorptions that characterize an acceptable whole blood sample. Second, absorbance at 660 nm must reach a constant value ("end point") within the maximum time permitted by the meter software. Third, the 660 nm end point absorbance value must be achieved consistently by a properly functioning meter and strip.

The above criteria can be met by an aqueous dispersion of opaque particles, such as iron oxide or carbon particles, and a predetermined concentration of glucose. Carbon particles are preferred, and in order for the absorption of 940 nm radiation to be great enough to indicate to the meter that sample size is adequate, carbon particle concentration is preferably at least about 0.015% w/v. Carbon particles that are substantially spherical and have a diameter of about 40 nm are suitable. A suspension of activated charcoal could be used, but a preferred carbon particle suspension is HIGGINS® black india ink, available from Faber-Castell Corp., Newark, N.J.

For reasons that are not entirely clear, end point stability is affected by ionic strength. Thus, to ensure a stable end point (constant 660 nm radiation detected), the control solution preferably includes a stabilizer, such as chloride or borate ion. Preferably, chloride ion is used and its concentration is in the range from about 0.1% to about 0.25% w/v, more preferably about 0.20% w/v. The chloride ion is conveniently provided by a metal salt, such as sodium or potassium chloride. Alternative stabilizers include sodium tetraborate and boric acid.

Preferably, pH of the control solution is maintained in the range from about 6.5 to 7.5. At lower pH, the carbon tends to precipitate. At higher pH, the long term stability of glucose in solution decreases. To maintain the preferred pH range, the solution preferably includes a buffer, such as citrate or EDTA di- and tetra-sodium. EDTA is preferred.

The glucose concentration indicated by the meter when a control solution is applied to a strip need not be the actual glucose concentration of the control solution; in fact, it generally is not. However, a control solution should consistently provide the same reading of glucose concentration when used with a fresh strip and a properly operating meter. In practice, it may be desirable to have control solutions that have different glucose concentrations; for example "high", "normal", and "low" glucose solutions, so that the full range of meter operation can be monitored. The appropriate control solution glucose concentration for each range is determined empirically. In order to ensure that control solutions yield reliable readings, solution stability is important. Low temperature stability is enhanced by including an antifreeze, such as diacetone alcohol or glycerol. Glycerol is preferred.

Preservatives may also be added to the control solution. Possible preservatives include sodium- or potassium-benzoate, benzalkonium chloride, chlorhexidine, and imidazolidinyl urea (for example, GERMALL® II, available from Sutton Laboratories, Chatham, N.J.). Preferably, at least about 0.07% w/v imidazolidinyl urea is included.

For a better understanding of the present invention, the following Example further illustrates the invention. The Example is not intended to be in any way limiting.

EXAMPLE

A control solution was prepared by combining the following components:

HPLC grade water 100 mL glycerol 1.2 g disodium EDTA 0.125 g tetrasodium EDTA 0.075 g GERMALL® II 0.2 g NaCl 0.2 g D-glucose 0.082 g HIGGINS® india ink (6% carbon black) 0.38 mL The control solution simulated blood that contains a "normal" glucose concentration (about 120 mg/dL). Control solutions that simulate high and low glucose concentrations include more or less D-glucose, respectively.

It will be understood by those skilled in the art that the foregoing description and Example are illustrative of practicing the present invention but are in no way limiting. Variations of the detail presented herein may be made without departing from the scope and spirit of the present invention.

We claim:

1. The control solution that mimics whole blood for use with a photometric blood glucose strip, which comprises a suspension of opaque iron oxide or carbon water, a dispersant to keep the particles in suspension, and a predetermined concentration of glucose.

2. The control solution of claim 1 in which the opaque particles comprise carbon particles.

3. The control solution of claim 2 in which the concentration of particles is at least about 0.015% w/v.

4. The control solution of claim 2 in which the particles are substantially spherical, with a diameter of about 40 nm.

5. The control solution of claim 1 further comprising an end point stablizer, which stablizes absorbance of 660 nm radiation by the control solution a predetermined time after contact with a photometric blood glucose strip.

6. The control solution of claim 5 in which the end point stabilizer is chloride ion.

7. The control solution of claim 6 in which the chloride ion concentration is in a range from about 0.1% to about 0.25% w/v.

8. The control solution of claim 7 in which the chloride ion concentration is about 0.20% w/v.

9. The control solution of claim 1 further comprising a buffer.

10. The control solution of claim 9 in which the buffer comprises EDTA.

11. The control solution of claim 9 in which the buffer maintains the solution at a pH in a range from about 6.5 to about 7.5.

12. The control solution of claim 1 further comprising an antifreeze.

13. The control solution of claim 12 in which the antifreeze comprises glycerol.

14. The control solution of claim 1 further comprising a preservative.

15. The control solution of claim 14 in which the preservative is imidazolidinyl urea.

16. The control solution of claim 15 in which the imidazolidinyl urea concentration is at least about 0.07% w/v.

* * * * *